United States Patent [19]

Cahiez et al.

[11] Patent Number: 5,426,201
[45] Date of Patent: Jun. 20, 1995

[54] PREPARATION OF MANGANOUS ENOLATES AND ITS APPLICATIONS

[75] Inventors: Gérard Cahiez; Patrick Clery, both of Paris; Jean-Alex Laffitte, Pau, all of France

[73] Assignee: Societe Nationale Elf Aquitaine, Courbevoie, France

[21] Appl. No.: 211,261

[22] PCT Filed: Sep. 21, 1992

[86] PCT No.: PCT/FR92/00877
§ 371 Date: Apr. 25, 1994
§ 102(e) Date: Apr. 25, 1994

[87] PCT Pub. No.: WO93/06071
PCT Pub. Date: Apr. 1, 1993

[30] Foreign Application Priority Data

Sep. 25, 1991 [FR] France .................... 91 11814

[51] Int. Cl.[6] .................. C07F 13/00; C07C 45/00
[52] U.S. Cl. ........................ 556/45; 568/312; 568/343
[58] Field of Search ................ 556/45; 568/312, 343

[56] References Cited

FOREIGN PATENT DOCUMENTS 2639939 6/1990 France .

Primary Examiner—José G. Dees
Assistant Examiner—Porfirio Nazario-Gonzalez
Attorney, Agent, or Firm—Ostrolenk, Faber, Gerb & Soffen

[57] ABSTRACT

A method of preparing manganous enolates by the treatment of alkali metal or alkaline earth metal enolates with manganous compounds in a solvent for the Mn enolate to be prepared.

16 Claims, No Drawings

PREPARATION OF MANGANOUS ENOLATES AND ITS APPLICATIONS

This application is a request for U.S. examination filed under 35 USC 371 of International application No. PCT/FR92/000877 filed on Sep. 21, 1992.

The invention relates to a novel method of preparing manganous enolates and to its applications.

The utility of enolates in general is well recognized, particularly since the work by FLEMING et al. ("Synthesis" 1976, 736, and "Chem. Soc. Rev." 1981, 10, 83); these compounds are used especially as intermediates in different chemical reactions. They make it possible, for example, to obtain various esters, ketones or aldehydes which are useful in perfumery or as starting materials for the production of drugs or pesticides. Particularly valuable enolates, namely manganous enolates, form the subject of a French patent application published under no. 2 639 939. According to said document, manganous enolates are prepared by reacting mixed organomanganous compounds with ketones.

The advantages of Mn enolates include, for example, that of avoiding the polyalkylation or polyalkarylation of the ketone when these enolates are reacted with alkyl or alkaryl halides; by contrast, alkali metal and alkaline earth metal enolates, in particular lithium enolates, lead to a greater or lesser degree of polyalkylation or polyalkarylation. On the other hand, certain organomanganous compounds, particularly amides prepared by the method referred to above, give relatively inadequate yields in some of their applications, such as esterification or silylation reactions.

The present invention provides an improvement which, while retaining the advantage of avoiding polyalkylation or polyalkarylation, makes it possible substantially to increase the yield of reactions where organomanganous compounds were somewhat deficient.

The method according to the invention for the preparation of manganous enolates comprises treating an alkali metal or alkaline earth metal enolate with a manganous compound in a solvent for the Mn enolate to be prepared.

As alkali metal and alkaline earth metal enolates and their preparation are known, it is not necessary to describe them in detail here, suffice it to say that they are usually compounds of Na, K, Li, Ca or Mg, especially Li. Their preparation consists in reacting a corresponding organometallic compound with an organic compound carrying at least one carbonyl, particularly a ketone. The reaction is carried out in a solvent, generally at between −78° C. and +100° C., room temperature being suitable in many cases.

The reaction according to the invention, which constitutes a transmetalation, can be represented as follows:

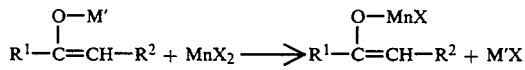  (1)

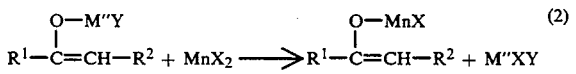  (2)

or

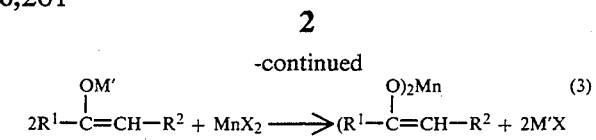  (3)

M' being a monovalent metal, M" being a divalent metal and it being possible for X and Y, which are identical or different, to be non-oxidizing anions or amino groups. $MnX_2$ can be replaced with YMnX. Manganous halides, especially $MnCl_2$, are suitable as $MnX_2$.

Lithium enolates, where M' is Li, are particularly suitable.

In general, depending on the nature of the compounds involved, the temperature of the reaction medium is adjusted so as not to affect the stability of the reactants and so as to obtain the desired product in a reasonable period of time, for example in 0.3 to 3 hours. The preferred temperatures range between about −78° and +100° C. and in particular from 10° C. to 50° C.; one of the advantages of the method is that room temperature is suitable in many cases, it being possible for the reaction to be completed in about 0.5 to 2 hours at temperatures of 15° to 30° C.

The molar ratios of the reactants according to reaction (1) or (2) indicated above are usually stoichiometric, but it can be useful to employ an excess of manganous salt $MnX_2$ of, for example, 0 to 100% relative to stoichiometry, i.e. 1 to 2 mol per mol of enolate, but a deficiency thereof for reaction (3).

The method of the invention can be carried out with various concentrations of the reactants in the solvent used; the preferred concentrations range between about 0.1 and 2 mol or, preferably, between 0.2 and 0.8 mol of the compound carrying the carbonyl group per liter of solvent.

Ethers, especially diethyl ether, pyran, 1,2-dimethoxyethane and particularly tetrahydrofuran, may be mentioned among the principal solvents which can be used; it is also possible to employ dimethyl sulfoxide or sulfolane, other solvents being within the scope of those skilled in the art. It is sometimes possible to improve the solubility of the manganous salt $MnX_2$ in the solvent by the addition of an alkali metal salt, in particular an Li salt, as is practiced in the art.

The method of the invention is applicable to alkali metal and alkaline earth metal enolates derived from numerous ketones. Linear aliphatic ketones such as $CH_3(CH_2)_n-CO-(CH_2)_m CH_3$, in which the numbers n and m, which are identical or different, are 0 to 17, are suitable among the corresponding monoketones. Furthermore, in one or each of their chains $(CH_2)_n$ and $(CH_2)_m$, there can be a double or triple bond and/or an alkyl or aryl substituent. Similar ketones carry a secondary or tertiary group, i.e.

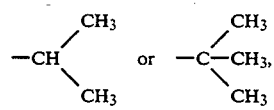

in place of one or both of the terminal $CH_3$ groups. It is also possible to use enolates of ketones in which one or both of the chains $CH_3(CH_2)_n$ or $CH_3(CH_2)_m$ are replaced with a phenyl, tolyl, xylyl, naphthyl, cyclopentyl, cyclohexyl or cyclohexenyl ring which can carry one or more alkyl substituents. The starting ketones can carry functional groups (halogens, alkoxy, thioalkoxy, etc.).

By way of non-limiting examples, the invention can be carried out starting from enolates corresponding to ketones like diethyl ketone, dipropyl ketone, diisopropyl ketone, ethyl propyl ketone, ethyl hexyl ketone, ethyl cyclohexyl ketone, ethyl phenyl ketone, butylcyclopentanone, methylcyclohexanone, hexyl heptyl ketone, butyl dodecyl ketone, acetophenone, etc.

The foregoing statements regarding the ketones define the nature of the groups $R^1$ and $R^2$ in reactions (1) and (2) illustrated above. Thus, while $R^2$ can be H, $R^1$ and $R^2$, which are identical or different, can consist of $C_1$ to $C_{20}$, preferably $C_1$ to $C_{12}$, alkyl, alkenyl or alkynyl chains which can comprise aryl substituents, or cycloalkyls, in particular cyclopentyl or cyclohexyl, which can carry one or more $C_1$ to $C_{12}$ alkyl substituents; aryl rings, in particular phenyl or naphthyl, which can optionally carry 1 to 3 $C_1$ to $C_{12}$ substituents, are suitable; phenyl, tolyl, xylyl, mesityl, mono-, di- or tri-ethylphenyl, dipropylphenyl, etc. thus form valuable enolates.

In the manganous compound $MnX_2$, X can be a halogen or a non-oxidizing anion of a compound of S, P, B, C or Si, an oxy- or thia-hydrocarbon group, an amino group, etc. Thus, for example, X is Cl, Br or I, $CF_3$—$SO_2$, R'COO, $BF_4$, —OR' or —SR' (R' being an alkyl or aryl) —$NR'_2$ or —NR'R", R' and R" being hydrocarbon groups, mainly $C_1$ to $C_{12}$ alkyl groups and/or $C_6$ to $C_{10}$ aryl groups.

The manganese enolate formed can be recovered from the reaction medium by evaporation of the solvent in the absence of air and moisture, or by any other known means, and can then be converted to the desired derivative. However, in the majority of common applications, this enolate can easily be treated in situ, in its original solvent, with the optional addition of another solvent and/or modification of the temperature, before a new appropriate reactant is introduced. The product can thus be acylated, silylated, alkylated, halogenated, hydroxyalkylated, etc., in its reaction medium, by the addition of an acid anhydride or chloride, a trialkylsilyl halide, an allyl or alkyl halide, a halogen or an aldehyde, followed by water, etc. As the manganese is eliminated during such reactions, the final products are esters of the enols in question, β-diketones, silylated derivatives or the corresponding alkylated, allylated or halogenated ketones, etc. The starting ketone can likewise be aldolized.

EXAMPLE 1

Preparation of a manganous enolate corresponding to dipropyl ketone and its application to the α-benzylation thereof The starting material is the corresponding lithium enolate:

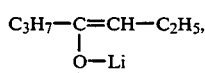

obtained by reacting Li diisopropylamide, i.e.:

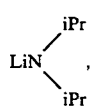

with dipropyl ketone:

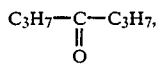

at room temperature.

A. - 125 mmol of $MnCl_2$ in the form of its double salt $MnCl_2 \cdot 2LiCl$, in 200 ml of THF, are added to a solution of 100 mmol of Li enolate in 150 ml of tetrahydrofuran (THF). The mixture is stirred for 1 hour at 20° C., resulting in transmetalation:

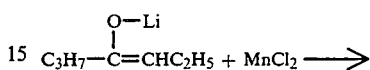

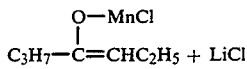

125 mmol of benzyl bromide, $PhCH_2Br$, and 75 ml of dimethyl sulfoxide (DMSO) are added dropwise to the solution obtained. After stirring for 1 hour at 20° C., the formation of dipropyl ketone benzylated in the α-position to the ketone functional group is observed with a yield of 94% relative to the starting heptanone.

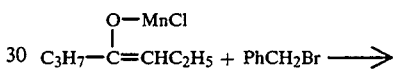

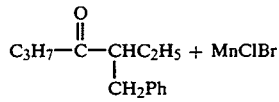

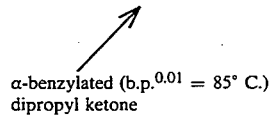

α-benzylated (b.p.$^{0.01}$ = 85° C.) dipropyl ketone

No polybenzylation takes place.

B. - The starting material is the same Li enolate as in A but, instead of carrying out a transmetalation, the benzyl halide is reacted immediately by stirring 100 mmol of the Li enolate in 150 ml of THF with 125 mmol of $PhCH_2Br$ and 75 ml of DMSO for 1 hour at 20° C. The following reaction takes place:

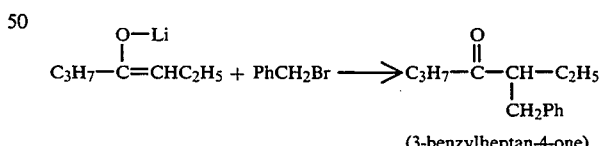

(3-benzylheptan-4-one)

but the benzylated ketone is thus obtained with a yield of only 68% (compared with 94% in A) and is accompanied by polybenzylated products formed at a rate of 23%, these products being of the type

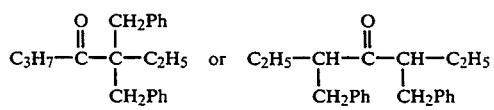

It can thus be seen that the conversion of the Li enolate to the Mn enolate has brought marked advantages.

EXAMPLE 2

Preparation of a manganous enolate and its silylation

A. - One experiment consisted in starting from an Mn enolate prepared not by the direct reaction of an organo-Mn compound with cyclohexanone but by transmetalation from the lithium enolate in a manner similar to A of Example 1:

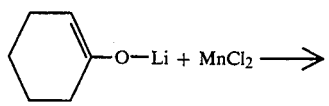

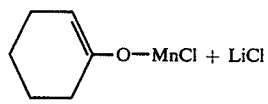

Silylation, performed as under B (see below), is then carried out with a yield of 77%.

B. - In another experiment, an enolate is prepared by the reaction of 100 mmol of phenylmanganese N-methyl-N-phenylamide:

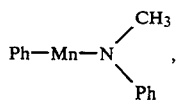

with 100 mmol of cyclohexanone in 200 ml of THF at 20° C. for 1 hour:

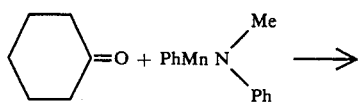

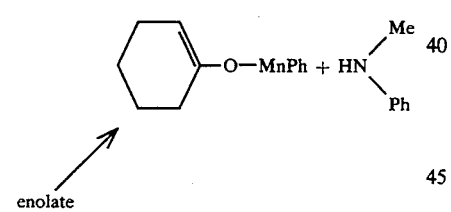

100 mmol of trimethylchlorosilane, ClSiMe$_3$, are added to the resulting solution at 20° C. and the mixture is stirred for 30 minutes to produce the following reaction:

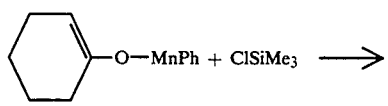

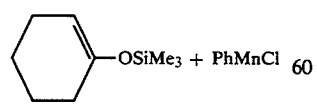

1-Trimethylsilyloxycyclohexene is obtained with a yield of 59%, compared with 77% for procedure A.

EXAMPLE 3

Preparations analogous to those of Example 2 are carried out starting from 3-methylcyclohexanone instead of cyclohexanone. The procedure in B is the same, starting from

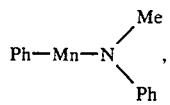

but the procedure in A is transmetalation of the lithium enolate to the manganous enolate. Silylation is then carried out with yields of
79% for A
and 67% for B.

EXAMPLE 4

Experiments similar to those of Examples 2 and 3 are performed starting from nonanone:

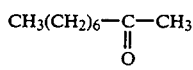

The yields of silylated compound:

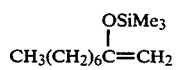

are as follows in this case:
for A - 78%
for B - traces.

The advantage of transmetalation to give the manganous enolate appears to be particularly marked for the products derived from ketones possessing a methyl in the α-position to the carbonyl.

EXAMPLES 5 to 7

The technique of Example 1, A and B, was applied to the preparation of an Mn enolate from cyclohexanone, 2-methylcyclohexanone and 3-methylcyclohexanone. Each of these Mn enolates was then alkylated with benzyl bromide, C$_6$H$_5$CH$_2$Br, by comparison with the same alkylation applied to the corresponding lithium enolate. The Table below gives the % yields of the benzylated ketone obtained and the % polybenzylation.

| Ex. | Method | Starting ketone | Enolate of | Yield % | % polyalkylation |
|---|---|---|---|---|---|
| 5 | A | cyclohexanone | Mn by transmetalation | 88 | 0 |
| 5 | B | " | Li | 55 | 32 |
| 6 | A | 2-methylcyclohexanone | Mn by transmetalation | 85 | 0 |
| 6 | B | 2-methylcyclohexanone | Li | 65 | 25 |
| 7 | A | 3-methylcyclohexanone | Mn by transmetalation | 79 | 0 |
| 7 | B | 3-methylcyclohexanone | Li | 37 | 47 |

Compared with those of Example 1, these results show that the yield is improved by the invention, both for the linear starting ketones and for the cyclic ketones, the same applying to polyalkylation. This is completely suppressed in the method according to the invention,

EXAMPLE 8

Application to the aldolization of a ketone

Transmetalation of the lithium enolate derived from pentanone was used to prepare the manganous enolate in a manner analogous to that of Example 1-A:

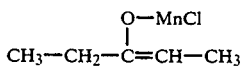

$$CH_3-CH_2-\underset{\underset{\displaystyle O-MnCl}{|}}{C}=CH-CH_3$$

100 mmol of benzaldehyde, $C_6H_5CHO$, were mixed in 1 minute at $-78°$ C. with 200 ml of THF containing 100 mmol of the above compound. This was followed by reaction with water:

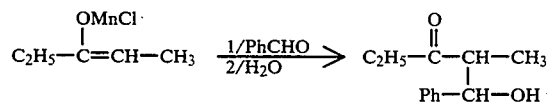

EXAMPLE 9

Application of the invention to the aldolization of a ketone 50 mmol (5.1 ml) of benzaldehyde are added at $-78°$ C. to the manganous enolate of diethyl ketone, prepared by the procedure described above. After stirring for 10 seconds at $-78°$ C., the reaction medium is hydrolyzed by the dropwise addition of a saturated solution of $(NH_4)_2SO_4$. After decantation, filtration on hyflo-supercel and evaporation of the solvents under vacuum, 5-phenyl-5-hydroxy-4-methylpentan-3-one is isolated by low pressure liquid chromatography on 15 μm silica gel using cyclohexane/ethyl acetate (90/10) as the eluent. Yield=72%. Erythro/threo=61/39.

EXAMPLE 10

Preparation of a manganous enolate of an ester 50 mmol of BuLi/hexane are added at $-30°$ C. to a solution of 50 mmol (5.05 g) of diisopropylamine in 60 ml of THF. The reaction medium is stirred at room temperature for 30 minutes, after which 40 mmol (4.08 g) of ethyl propionate are added dropwise over 15 minutes at $-78°$ C. Stirring is maintained for 15 minutes at this temperature and a solution of 50 mmol (10.55 g) of the complex $MnCl_4Li_2$ in 80 ml of THF is then added dropwise over 10 minutes. The reaction medium is stirred at room temperature for 30 minutes (orange coloration).

EXAMPLE 11

Aldolization of an ester 50 mmol (5.10 ml) of benzaldehyde are added at $-78°$ C. to the manganous enolate of ethyl propionate, prepared as indicated above. After stirring for 10 seconds at $-78°$ C., the reaction medium is hydrolyzed by the dropwise addition of a saturated solution of $(NH_4)_2SO_4$. After decantation, filtration on hyflo-supercel and evaporation of the solvents under vacuum, ethyl 3-phenyl-3-hydroxy-2-methylpropionate is isolated by low pressure liquid chromatography on 15 μm silica gel using cyclohexane/ethyle acetate (90/10) as the eluent. Yield=72%. Erythro/threo=61/39.

whereas it takes on substantial proportions in the prior art, as moreover indicated by H. HOUSE in Organic Syntheses Cell. vol. VI, 1988, 121, and by H. HOUSE et al. in J. Org. Chem. 1971, 36, 2361.

What is claimed is:

1. A method of preparing manganous enolate, which comprises contacting alkali metal or alkaline earth metal enolate with manganous compound in a solvent for the Mn enolate to be prepared.

2. A method according to claim 1 wherein the contacting, which constitutes a transmetalation, is of the enolate by means of an Na, K, Li, Ca or Mg enolate.

3. A method according to claim 1 wherein the manganous compound is of the formula $MnX_2$ or $YMnX$, X and Y being identical or different non-oxidizing anions or amino groups.

4. A method according to claim 1 wherein the treatment is effected at between $-78°$ C. and $+100°$ C., in 0.3 to 3 hours.

5. A method according to claim 1 wherein the molar ratio manganous compound/enolate is 0.5 to 2.

6. A method according to claim 1 wherein each of the reactants is present in the solvent at a concentration of 0.1 to 2 mol per liter of solvent.

7. A method according to claim 1 wherein the enolate subjected to transmetalation is

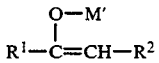

$$R^1-\underset{\underset{\displaystyle O-M'}{|}}{C}=CH-R^2 \quad (1)$$

or

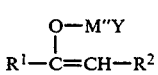

$$R^1-\underset{\underset{\displaystyle O-M''Y}{|}}{C}=CH-R^2 \quad (2)$$

M' being an alkali metal, M" being an alkaline earth metal, Y being a non-oxidizing anion or an amino group and $R^1$ and $R^2$, which are identical or different, being $C_1$ to $C_{20}$ alkyl, alkenyl or alkynyl optionally aryl substituted, or cycloalkyl, optionally $C_1$ to $C_{12}$ alkyl substituted or $C_6$ to $C_{10}$ aryl, it also being possible for $R^2$ to be a hydrogen atom.

8. A method according to claim 7 in which M' is lithium.

9. In a method of preparing an acylated, silylated, alkylated, halogenated or hydroxyalkylated enol comprising forming a manganous enolate and reacting the enolate with an acid anhydride or a halide, the improvement which comprises forming the enolate utilizing the method of claim 1.

10. In a method of preparing an acylated, alkylated, halogenated, allylated or hydroxyalkylated ketone comprising forming a manganous enolate and reacting the enolate with a halide, halogen or aldehyde, the improvement which comprises forming the enolate utilizing the method of claim 1.

11. Method according to claim 10 wherein firstly a ketone is reacted with an organic lithium derivative in a solvent to form an Li enolate, the solution is then stirred with a manganese salt and the resulting solution of Mn enolate is mixed with an alkyl, alkaryl or aryl halide so as to attach a single alkyl, alkaryl or aryl to the starting ketone.

12. A manganeous dienolate of the formula

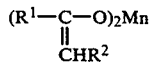

$$(R^1-\underset{\underset{\displaystyle O}{||}}{C}-O)_2Mn$$
$$|$$
$$CHR^2$$

in which $R^1$ and $R^2$, which are identical or different, being $C_1$ to $C_{20}$ alkyl, alkenyl or alkynyl optionally aryl substituted, or cycloalkyl, optionally $C_1$ to $C_{12}$ alkyl substituted or $C_6$ to $C_{10}$ aryl, it also being possible for $R^2$ to be a hydrogen atom.

13. A dienolate according to claim 12 in which the alkyl, alkenyl or alkynyl group has 1 to 12 carbon atoms and the cycloalkyl group has 5 or 6 carbon atoms.

14. A method according to claim 2 in which the enolate is a lithium enolate.

15. A method according to claim 4 in which the treatment is effected at between 10 and 50° C. for 0.5 to 2 hours.

16. A method according to claim 7 in which the alkyl, alkenyl or alkynyl group contains 1 to 12 carbon atoms and the cycloalkyl group contains 5 or 6 carbon atoms.

* * * * *